United States Patent
Tseng et al.

(10) Patent No.: US 8,932,874 B2
(45) Date of Patent: Jan. 13, 2015

(54) CONTROL OVER AMMONIUM FLUORIDE LEVELS IN OXIDE ETCHANT

(71) Applicant: Nalco Company, Naperville, IL (US)

(72) Inventors: Amy M. Tseng, Woodridge, IL (US); Brian V. Jenkins, Warrenville, IL (US); Robert M. Mack, Milwaukie, OR (US)

(73) Assignee: Nalco Company, Naperville, IL (US)

( * ) Notice: Subject to any disclaimer, the term of this patent is extended or adjusted under 35 U.S.C. 154(b) by 0 days.

(21) Appl. No.: 14/322,009

(22) Filed: Jul. 2, 2014

(65) Prior Publication Data

US 2014/0315320 A1   Oct. 23, 2014

Related U.S. Application Data

(60) Continuation of application No. 14/082,448, filed on Nov. 18, 2013, now abandoned, which is a division of application No. 13/731,296, filed on Dec. 31, 2012, now Pat. No. 8,716,028, which is a continuation-in-part of application No. 11/696,797, filed on Apr. 5, 2007, now Pat. No. 8,372,651.

(51) Int. Cl.
  *G01N 21/75* (2006.01)
  *G01N 31/22* (2006.01)
  (Continued)

(52) U.S. Cl.
  CPC ............ *G01N 31/221* (2013.01); *G01N 35/085* (2013.01); *B81C 2201/0132* (2013.01);
  (Continued)

(58) Field of Classification Search
  CPC ................ H01L 21/67063; B81C 2201/0142; B81C 1/00531; B81C 2201/0132; C09K 13/00; G01N 35/085
  USPC ......... 422/400, 401, 402, 403, 404, 420, 421, 422/422, 423, 424, 425, 426, 427, 428, 429, 422/68.1, 75, 76, 77, 82.05, 82.06, 82.07, 422/82.08, 82.09, 82.11; 436/164, 165, 436/166, 169, 170, 171, 172; 435/13, 435/283.1, 287.1, 287.7, 287.8, 287.9, 435/288.7; 134/2, 3; 438/5, 6, 7, 8, 9, 16, 438/27, 29
  See application file for complete search history.

(56) References Cited

U.S. PATENT DOCUMENTS

| | | | |
|---|---|---|---|
| 6,406,641 B1 | 6/2002 | Golzarian | |
| 6,617,165 B1 | 9/2003 | Opitz et al. | |

(Continued)

FOREIGN PATENT DOCUMENTS

| | | |
|---|---|---|
| KR | 1020010065793 A | 7/2001 |
| KR | 100700280 B1 | 3/2007 |
| KR | 100860269 B1 | 9/2008 |

OTHER PUBLICATIONS

Karen A. Reinhardt, et al., Handbook of Silicon Wafer Cleaning Technology (2nd Edition), 2008, p. 23.

(Continued)

*Primary Examiner* — Dennis M White
(74) *Attorney, Agent, or Firm* — Benjamin E. Carlsen

(57) ABSTRACT

The invention is directed towards methods and compositions for identifying the amount of ammonium acid in a buffered oxide etching composition. In buffered oxide etching compositions it is very difficult to measure the amount of ammonium acid because it has varying equilibriums and it is toxic so it hard to handle and sample. When used to manufacture microchips however, incorrect amounts of ammonium acid will ruin those chips. The invention utilizes a unique method of spectrographically measuring the ammonium acid when in contact with added chromogenic agents to obtain exact measurements that are accurate, immediate, and safe.

12 Claims, 9 Drawing Sheets

(51) Int. Cl.
*G01N 35/08* (2006.01)
*B81C 1/00* (2006.01)
*H01L 21/67* (2006.01)
*C09K 13/00* (2006.01)

(52) U.S. Cl.
CPC ....... *B81C1/00531* (2013.01); *H01L 21/67063* (2013.01); *B81C 2201/0142* (2013.01); *C09K 13/00* (2013.01)
USPC .......... 436/166; 436/164; 436/165; 436/169; 436/170; 436/171; 436/172; 422/400; 422/401; 422/402; 422/403; 422/420; 422/421; 422/422; 422/423; 422/424; 422/426; 422/425; 422/428; 422/429; 422/68.1; 422/75; 422/76; 422/77; 422/82.05; 422/82.06; 422/82.07; 422/82.08; 422/82.09; 422/82.11; 435/13; 435/283.1; 435/287.1; 435/287.7; 435/287.8; 435/287.9; 435/288.7; 134/2; 134/3; 438/5; 438/6; 438/7; 438/8; 438/9; 438/16; 438/27; 438/29

(56) References Cited

U.S. PATENT DOCUMENTS

| | | |
|---|---|---|
| 6,716,362 B1 | 4/2004 | Benz |
| 6,716,391 B1 | 4/2004 | Olson |
| 6,849,463 B2 | 2/2005 | Santini et al. |
| 7,019,850 B2 | 3/2006 | Finarov |
| 7,306,696 B2 | 12/2007 | Lian et al. |
| 7,928,368 B2 | 4/2011 | Nissila et al. |
| 8,029,730 B1 | 10/2011 | Olson et al. |
| 8,071,390 B2 | 12/2011 | Tokhtuev et al. |
| 8,222,079 B2 | 7/2012 | Knickerbocker et al. |
| 2001/0037820 A1 | 11/2001 | Jenkins et al. |

OTHER PUBLICATIONS

W. Kern, Thin Film Processes, 1978, Chapter V-1, Academic Press.

Website: http://www.flowinjection.com/29.%20Principle%20-%20Flow%20Injection.html, Dec. 10, 2012.

Website: http://www.flowinjection.com/30.%20Principle%20-%20Sequential%20Injection.html, Dec. 10, 2012.

Jorg Acker, et al., Chemical analysis of acidic silicon etch solutions II. Determination of $HNO.$, HF and $H_2SiF_6$ by ion chromatography, ScienceDirect, Talanta 72 (2007) pp. 1540-1545.

Honeywell, Apr. 2001, Modified and Improved BOEs pp. 1-20.

International Search Report mailed Apr. 25, 2014 for related PCT application PCT/US2013/077328. (10 Pages).

CONTROL OVER AMMONIUM FLUORIDE LEVELS IN OXIDE ETCHANT

CROSS-REFERENCE TO RELATED APPLICATIONS

This application is a continuation of U.S. patent application Ser. No. 14/082,448 filed on Nov. 18, 2013 which is a divisional application of co-pending U.S. patent application Ser. No. 13/731,296 which was filed on Dec. 31, 2012 which itself was a continuation in part of U.S. patent application Ser. No. 11/696,797 which was filed on Apr. 5, 2007 and has issued as U.S. Pat. No. 8,372,651.

STATEMENT REGARDING FEDERALLY SPONSORED RESEARCH OR DEVELOPMENT

Not Applicable.

BACKGROUND OF THE INVENTION

The present invention relates generally to compositions of matter, apparatuses and methods useful in detecting, identifying, and measuring the precise amount of Hydrogen Fluoride (HF) in a sample of Oxide Etchant used in the manufacture of micro-electronic components.

As described for example is U.S. Pat. Nos. 7,928,368, 6,849,463, and 8,222,079, in the manufacture of micro-electronic components it is quite common to etch the wafer substrate of those components. Etching is the process of removing silicon containing substrate material from the wafer, especially from its surface. Etching commonly involves removing discrete amounts of silicon (or other) material from the wafer to expose other materials layered in the wafer such as buffers, masks, and/or insulation. Etching is also performed to clean the wafer surface, to polish the wafer surface to a desired degree of smoothness, and/or to create reservoirs or channels in the substrate for thermal or electrical shielding purposes or into which devices or other materials can be placed. Etching is a very precise process and it only removes the specific targeted material and/or desired shape in the substrate. In fact Etching can be fully isotropic but sometimes is also anisotropic.

Etching is often performed by a number of processes including the use of high temperature plasma and chemicals such as buffered oxide etchants (BOE). A commonly used buffered oxide is a composition comprising HF such as $HF$—$HNO_3$ mixtures and/or $HF$—$NH_4F$ mixtures. These HF bearing mixtures are used because it is highly isotropic for silicon, the most common material used in wafer substrates. Unfortunately using HF involves very low tolerances for dosage errors. This is because the magnitude of the amount of silicon etched away by an HF application alters dramatically with even slight changes in the concentration of HF in a given applied dosage. This intolerance is compounded by the fact that the wafer material and targeted etches are micro-scale in size so even slight alterations in silicon removal amounts can utterly ruin the would-be micro-electronic component. As a result, it is extremely important to have highly accurate measurements of the actual amounts of HF species present in the etching composition being used.

In addition, as described in the scientific paper *Chemical Analysis of Acidic Silicon Etch Solutions II. Deteremination of $HNO_3$, HF, and $H_2SiF_6$ by Ion Chromatography*, by Jörg Acker, Talanta Volume 72, pp. 1540-1545 (2007), HF and nitrogen bearing species in the composition undergo highly complex equilibrium mechanisms and are also highly toxic and difficult to handle. This makes it impractical and non-economic to use common industry analytical methods for reliably measuring HF levels in a sample.

In addition the intolerance, toxicity, and reactivity make common inventorying procedures impossible with HF etching compositions. Commercially prepared HF etching compositions come in a variety of dosages and concentrations. In normal manufacturing processes, the particular compositions purchased would be the optimal application of available supply and demand. The purchased compositions are then diluted and mixed using standard stoichiometric techniques to obtain a desired dosage concentration. This process however can't be done with HF containing BOE compositions because mixing two or more non-identical compositions results in losing knowledge regarding the exact concentration of HF (or at best it can only be done with cumbersome recordkeeping). Because of the low tolerances inherent in HF use, this results in industry avoiding mixing differently concentrated samples of HF and therefore incurring unwanted costs and inefficiencies.

Thus it is clear that there is definite utility in novel methods and compositions for the proper detection, identification, and measurement of HF in buffered oxide etching compositions. The art described in this section is not intended to constitute an admission that any patent, publication or other information referred to herein is "Prior Art" with respect to this invention, unless specifically designated as such. In addition, this section should not be construed to mean that a search has been made or that no other pertinent information as defined in 37 CFR §1.56(a) exists.

BRIEF SUMMARY OF THE INVENTION

At least one embodiment of the invention is directed towards a method of detecting and measuring the presence of a HF in a BOE composition. The method comprises the steps of: 1) collecting a representative sample of a BOE composition, 2) adding a chromogenic agent to the composition, 3) performing a spectrometric measurement of the composition, and 5) comparing the spectrometric measurement to pre-determined values to identify the quantity of HF in the BOE composition.

The method may include pre-determining the expected etch rate of a given BOE composition based on the interaction of temperature, surfactant type, surfactant concentration, HF concentration, composition flow rate, composition flow direction, and proximity of the location where the BOE composition will be applied to the location of a layer-layer interface on a wafer. Etching may occur by applying the BOE composition to the wafer. There may be simultaneous to etching, measuring the HF concentration with an SIA process using a chromogenic agent. There may be simultaneous to etching, measuring the surfactant concentration with an SIA process using a chromogenic agent. There may be simultaneous to etching, measuring the actual etch rate occurring using a laser reflectance. At least one of the temperature, surfactant type, surfactant concentration, HF concentration, composition flow direction, and composition flow rate to may be altered in response to the measurement to alter the actual etch rate to correspond to a desired etch rate.

The method may measure HF using an SIA process. The SIA process may included utilizing one mixture of dyes selected from the list consisting of phenol red with chlorophenol red, chlorophenol red with thymol blue, and phenol red with chlorophenol red and with thymol blue. Alcohol may also be added to the mixture. The amount of the mixture of dyes used in the SIA process may be insufficient to measure the concentration of HF if used in a non-sequential analytical process.

BRIEF DESCRIPTION OF THE DRAWINGS

A detailed description of the invention is hereafter described with specific reference being made to the drawings in which.

DETAILED DESCRIPTION OF THE INVENTION

Figure 1:
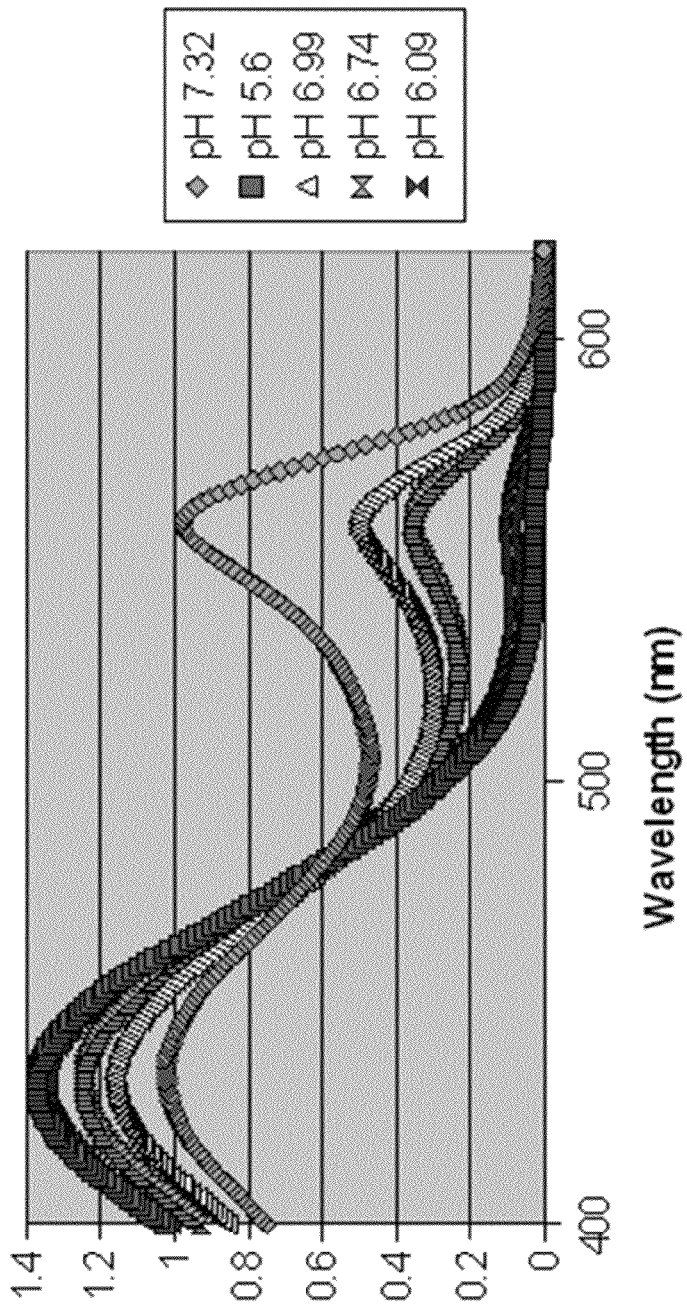
FIG. 1 is a graph illustrating the visible spectra of indicators in various pH buffers.

The following definitions are provided to determine how terms used in this application, and in particular how the claims, are to be construed. The organization of the definitions is for convenience only and is not intended to limit any of the definitions to any particular category.

"Buffered" means a liquid composition of matter characterized as containing a weak base and it conjugated acid and/or a weak acid and its congregated base in such an amount that it renders the liquid resistant to changes in pH.

"BOE" means buffered oxide etchant, it comprises ammonium fluoride, water, and hydrofluoric acid, representative examples of BOE are described in on page 23 of the textbook *Handbook of Silicon Wafer Cleaning Technology* (2nd Edition), edited by: Karen A. Reinhardt, et al., William Andrew Publishing (2008), and chapter V-1 of the textbook *Thin Film Processes*, by W. Kern et al., Academic Press, (1978).

"Complex" means one or more atoms, typically a metal (the core), bonded to a surrounding array of molecules (the ligands) via one or more bonding mechanisms including coordinate covalent bonds, dipolar bonds, and coordinated pi bonds. Metal complexes often have spectacular colors or have visible or invisible spectroscopic properties caused by electronic transitions in the complex often stimulated by the absorption of light or electromagnetic energy. These transitions often involve d-d transitions, where an electron in a d orbital on the core or ligand is readily excited by a photon to another d orbital of higher energy in an empty ligand or core-based orbital.

"Chromogenic Agent" means one or more compositions of matter which interact with a sample of matter to induce a change in interaction between the sample of matter and electromagnetic radiation that can be detected with Spectrometry. Chromogenic agents sometimes operate by forming transition changing complexes with the sample of matter.

"Etching" means applying an agent or process to a substrate to remove a pre-determined very specific very small amount of the substrate.

"FIA" means flow injection analysis, a form of chemical analysis accomplished by injecting a plug of sample into a continuous flow of a carrier fluid stream that mixes with other continuously flowing streams before reaching a detector. In some cases a sample mixes through radial and convection diffusion with a reagent also in the stream for a period of time (depending on the flow rate and the coil length and diameter) before the sample passes through a detector. Representative examples of FIA are described in the website entitled FIAlab Principle—Flow Injection having a URL of: http://www-.flowinjection.com/29.%20Principle%20-%20Flow%20Injection.html (as accessed on Dec. 10, 2012).

"SIA" means sequential injection analysis, a form of FIA which utilizes a programmable, bidirectional, discontinuous flow, precisely choreographed by computer control to optimize the specific reactivity conditions between a sample and a specific regent, typically a sample is introduced into a holding coil, followed by a volume of one or more reagents that is aspirated sequentially and thereby forms discrete zones in the stream. The stream is first moved in a first direction and is then reversed in direction which increases mixing and reactivity between the sample and the reagents, the reaction mixture then reaches a flow cell where the reaction product is monitored, this allows for processing of multiple samples with different properties in exactly the same way and allows for comparison of standards with unknowns. Representative examples of SIA are described in the website entitled FIAlab Principle—Sequential Injection having a URL of: http://www.flowinjection.com/30.%20Principle%20-%20Sequential%20Injection.html (as accessed on Dec. 6, 2012).

"SFA" means segmented flow analysis, a form of FIA in which the stream of material is divided by air bubbles into discrete segments in which different chemical reactions occur, the continuous stream of liquid samples and reagents are combined and transported in tubing and mixing coils from one analytical apparatus to another, the air bubbles segment each sample into discrete packets and act as a barrier between packets to prevent cross contamination between the segments as they travel down the length of the tubing, also the air bubbles assist mixing by creating turbulent flow (bolus flow), and they provide operators with a quick and easy check of the flow characteristics of the liquid.

"Spectrometry" and "Spectroscopy" means the process of analyzing the interaction between a sample of matter and electromagnetic radiation to determine one or more physical properties of the sample of matter. Forms of electromagnetic radiation used include but are not limited to one or more of microwave, terawave, infrared, near infrared, visible, ultraviolet, x-ray, radiation. The analysis includes measurements of one or more of the radiation's absorption, emission, fluorescence, colorometrics, color changes, reflection, scattering, impedance, refraction, and resonance by the sample of matter.

"Surfactant" is a broad term which includes anionic, nonionic, cationic, and zwitterionic surfactants. Enabling descriptions of surfactants are stated in *Kirk-Othmer, Encyclopedia of Chemical Technology*, Third Edition, volume 8, pages 900-912, and in *McCutcheon's Emulsifiers and Detergents*, both of which are incorporated herein by reference.

"Water Soluble" means materials that are soluble in water to at least 3%, by weight, at 25 degrees C.

In the event that the above definitions or a description stated elsewhere in this application is inconsistent with a meaning (explicit or implicit) which is commonly used, in a dictionary, or stated in a source incorporated by reference into this application, the application and the claim terms in particular are understood to be construed according to the definition or description in this application, and not according to the common definition, dictionary definition, or the definition that was incorporated by reference. In light of the above, in the event that a term can only be understood if it is construed by a dictionary, if the term is defined by the *Kirk-Othmer Encyclopedia of Chemical Technology*, 5th Edition, (2005), (Published by Wiley, John & Sons, Inc.) this definition shall control how the term is to be defined in the claims.

At least one embodiment of the invention is directed to a method of detecting the amount of HF present in a BOE. The steps of the method include: identifying the pH of an HF bearing liquid BOE, providing a composition of matter which at the identified pH functions as a chromogenic agent with HF, the chromogenic agent having different spectroscopic properties in the presence of HF than in the absence of HF, contacting the BOE with the agent, measuring the intensity of the change in spectroscopic properties, and correlating the observed change with a pre-established concentration of HF.

In at least one embodiment the method is conducted within an injection or flow system. As such, a flow of BOE enters a chamber, a flow of agent enters the chamber and a mixture of the two is then transported past a spectroscopic detector. In at least one embodiment the continuous injection system is an SIA, SFA, and/or FIA method such as those described in U.S. Pat. Nos. 8,071,390, 8,029,730, and 6,716,391.

FIA, SFA, and SIA are analytical techniques or systems that can perform wet chemical or bio-chemical reactions automatically along with detection of an analyte of interest. The flow injection technique may incorporate a pump, valves, and tubing to accommodate complicated chemical reactions that require reagents. The latest generation for FIA is SIA that uses very small (microliter (ul)) volumes of reagents and sample. It also uses a bidirectional syringe pump and a multiport selection valve. This technique is sometimes referred to as Lab-On-Valve (LOV). Reagents and sample can be drawn sequentially and "stacked" (sequentially injected) into a mixing coil (holding coil) before mixing while being pushed in a reverse direction into a detector (such as a spectrometer) for detection. The reagents and sample in the coil form the reaction product simultaneously and this reaction product flows into the detector. Appropriate to the chemical reaction desired, reagents, sample and mixing time can be controlled precisely with this technique. Hence, the analysis steps from sample introduction, chemical reaction, mixing, to detection are fully automated and precisely controlled with computer software. Reaction products can be detected by suitable detectors such as UV-VIS spectrometer, fluorescence spectrometer, Rayleigh light scattering, amperometer, etc. The SIA system is very flexible. SIA can be designed and formatted based on particular applications and the analyte of interest. Other adaptations include component separation or clean-up using a separation column. The technique is based on chemistry and chemical interaction. As FIA/SIA-LOV system uses very small amount of reagents and sample size, the reaction time and total analysis time are very fast (typically, a few minutes). This technique is applicable for on-line monitoring of components of interest in a continuous process using specific chemistry and detection techniques. In addition, multiple analytes can be measured accurately and simultaneously using different chemistries and system configurations.

By using FIA, SFA, and SIA the invention provides a method for reducing the amount of agent that needs to be added to a sample containing BOE to provide a given effect that is necessary for analysis of a sample. SIA also involves measurement of the sample. In some SIA systems the BOE and the agent are aspired into a holding coil in a first flow direction and are then transported in a second direction past a spectroscopic detector. The reversal of flow directions induces a rapid and highly efficient mixing effect.

In at least one embodiment, sampling utilizes a Lab-on-Valve module. In particular, the Lab-on-Valve module is associated with the process for making a microelectronic component. The Lab-on-Valve module serves as a platform upon which a sample can be drawn in, prepared for measurement, e.g. mixing with an agent, and for implementation of SIA or SFA analysis. An analytical measurement, such as pH of the sample, viscosity of the sample, or conductivity of the sample can be measured with the Lab-on-Valve module.

In at least one embodiment the spectrometric analysis used to detect and measure absorption peaks of emitted visible, IR, and UV light.

In at least one embodiment the chromogenic agent is one selected from the list consisting of phenol red, chlorophenol red, thymol blue, bromocresol green, bromocresol blue, thymol blue, rose Bengal, 4,5,6,7-Tetrachloro-2',4',5',7'-tetraiodofluorescein disodium salt, and any combination thereof.

In at least one embodiment the interaction between the HF and the agent induces an absorption peak at one or more of: 420 nm, 602 nm and/or 558 nm. In at least one embodiment the peaks have different intensities at the different wavelengths.

In at least one embodiment the correlation between the observed spectroscopic change and a pre-established concentration of HF involves determining an absorption peak for which the chromogenic agent and HF display along a pH range. The pH range can be as broad as 5-9 and even broader. In at least one embodiment the relationship between pH and the absorbance at the peak is linear.

In at least one embodiment the concentration of HF in the sample is so minute that it cannot be detected by other methods such as pH testing. In pH testing when a testing agent is added to the sample, a change in pH occurs. This change is caused by interactions between the HF and the testing agent and therefore its magnitude is directly related to the HF concentration. However if the concentration of HF is too low, the change in pH cannot be detected. In at least one embodiment the testing agent is at least one chromogenic agent. In at least one embodiment the spectrometric test is done as a check for or a pH test or in response to an inconclusive pH test. In at least one embodiment the concentration of HF in the sample is no more than 0.1%.

In at least one embodiment the BOE comprises a phosphate buffer.

In at least one embodiment the sample is in water.

In at least one embodiment the BOE comprises $H_2SiF_6$.

In at least one embodiment the sample is taken from a continuously fed process stream with varying sources of BOE. In a continuously fed process stream an etching applier is at various times fed with BOE which is then used in an etching process. Over time as the supply of BOE is partially consumed more BOE is added. The newly added BOE however may have a different concentration than the earlier fed BOE. As a result unless the exact amount of BOE that has been removed from the applier is known, stoichiometry cannot reveal what the exact concentration of HF is within the applier. In addition because of the complex equilibrium reactions, HF can react with the nitrogen bearing compounds in the BOE (especially $NH_4F$) and the amount of free HF at a given moment may not be consistent. As a result, in a continuously fed process stream, using the test method to measure the HF prior to etching will assure that the correct amount of HF is in the BOE regardless of how many different HF concentration BOEs are blended together. This allows for users to make use of common inventorying processes for BOE.

In at least one embodiment subsequent to determining the amount of HF present in a BOE sample, the specific amount of the BOE applied to a wafer is that which imparts the exact (or substantially the same) amount of HF needed for the desired amount of etching.

In at least one embodiment the etched substrate that the measured BOE sample is applied to is used to manufacture a: semiconductor chip, a microchip, a nano-electronic component, and any combination thereof.

In at least one embodiment the measurement of HF in BOE is performed in conjunction with a method of determining the amount of surfactant to be applied in conjunction with the BOE. Surfactants facilitate the dispersal of etchants applied to a substrate during an etching process. By doing so, a microelectronics manufacturer can achieve a more uniform and predictable result during the etching process. Precise control of the concentration of surfactant in the etchant can help achieve a more consistent outcome and therefore a need to monitor surfactants added to a microelectronic process is desired.

In at least one embodiment the spectroscopic measurement is conducted on a sample containing both surfactant and BOE. In at least one embodiment the surfactant interacts with the BOE to change the amount of free HF to be different than what was present in the absence of the surfactant.

In at least one embodiment the method of measuring the surfactant comprises the steps of: providing a surfactant whose UV-visible-IR absorbance can be determined, taking a sample from a process stream containing the surfactant into a flow cell, measuring the absorbance of the surfactant in the sample; correlating the absorbance of the surfactant in the sample with the concentration of the surfactant in the process. In at least one embodiment the method used to measure the surfactant is that described in U.S. patent application Ser. No. 13/525,395.

In at least one embodiment the effect the presence of HF has on the surfactant's absorbance and the effect the presence of surfactant has on the HF's absorbance is corrected for when measuring them.

In at least one embodiment the chromogenic agent used for the surfactant and for the HF is the same or is different.

In at least one embodiment the manufacturing method utilizes the measurements to assure that the ratio of surfactant volume to total volume of applied etching composition remains substantially at a ratio of 1:200.

In at least one embodiment the manufacturing method utilizes measurements in physical and or chemical properties of the etching composition to predict the instant etch rate of the composition. In at least one embodiment the manufacturing method utilizes the step of changing one or more of those physical and or chemical properties to change the etch rate to a more desired rate. Measuring the variables: BOE type, HF concentration, $NH_4F$ concentration, and temperature can be used to predict and control the overall etch rate. Because of the incredibly sensitive nature of etching compositions, changing one or more of these variables by even small amounts (like as little as: 20% or less in HF concentration, 7% or less in $NH_4F$ concentration, and/or 20° C. or less) can result in huge changes in etch rate such as up to or more than 350 nm/minute. By continuously keeping track of these variables the resulting etch rate can be predicted and the proper amount of etchant can be applied taking into account the changing conditions and applying the right amount of etchant accordingly.

In some cases the properties of etching compositions are altered if they undergo a temperature change and the properties do not in full or in part return even when the composition is returned to the original temperature. As a result special care must be taken in the storage and transport of the compositions to prevent their exposure to permanent or long term property changing effects due to temperature. In practice however sometimes manufactures do not know if in fact the composition has in fact never been exposed to a property changing temperature. In at least one embodiment the invention allows a user to determine the concentration of HF and/or other properties to determine the etch rate of an etching composition even if the composition was exposed to a property changing temperature or if such exposure cannot be otherwise determined.

As it gets diluted the buffering capacity of a BOE solution degrades and the effect changes in temperature have on the etch rate can be enormous. For example a well buffered BOE solution could react to a 2° C. increase in temperature with a 10 nm/minute increase in etch rate, but less buffered solution could respond to that same temperature increase with a 150 nm/minute increase in etch rate. In at least one embodiment the method uses the amount or changes in the amount of HF concentration to determine and/or change the buffering effectiveness of the BOE and the result that temperature (and changes in temperature) will have on etch rate.

In at least one embodiment the manufacturing method utilizes the measurements of free HF and/or surfactant to address undercutting. Wafers comprise layers of differing materials with fundamentally different properties. In some cases it has been determined that the type and/or amount of surfactant causes the etching composition to etch at a different rate in a location in a layer closer to the interface of two layers than it does farther away from the interface in that same layer. This results in more diagonally (sloping from the interface, relative to a vertical axis) walled voids as opposed to more vertically walled voids being formed by the etching composition. This resulting slanting geometry can be desirable or undesirable when it forms these undercutting voids. Because it is based on surface-surface interactions, undercutting is highly influenced by the types and amounts of surfactants present as wells as the free HF concentrations in the etching composition.

A representative method for understanding and addressing undercutting can be understood when etching an oxide layer adjacent to a photoresist layer. Photoresist is a layer of UV sensitive materials (typically comprising polymers) on the wafer which is highly photo sensitive to UV light. Oxide is a layer of oxidized silicon which is an effective insulator because of its low surface state charges. Oxide material closer to the oxide-photoresist interface is more readily etched than oxide material farther away from the oxide-photoresist interface. As a result etching oxide adjacent to photoresist can have a discrete diagonal slope. The slope will radically change (increase or decrease) in response to changes in one or more of: free HF concentration, etch rate, and surfactant concentration. In at least one embodiment one or more of the free HF concentration, etch rate, surfactant type, and/or surfactant amount, and any combination thereof in an etching composition is measured and altered to predict, cause, or prevent undercutting by at a wafer layer interface.

In at least one embodiment the very fast measurement of free HF concentration can be performed in conjunction and correlated with a very fast measurement of the rate of etching.

In at least one embodiment the method of etching involves determining the actual etch rate taking effect, determining the concentration of free HF and/or surfactant, and optionally changing one or more of spray rate of etching composition, free HF concentration, and surfactant concentration in response to the measurement. In at least one embodiment the very fast rate of measurement of the rate of etching is achieved by directing a light beam (such as a laser) at the wafer, measuring the intensity of the beam reflected off of the portion of the wafer being etched, and inferring from the reflected beam the thickness of the etched layer because the interference with the beam is directly dependent on the layer's thickness. Combining FIA, SIA or SFA measurement of HF and/or surfactant concentration with reflectance based measurements of etch rate (such as with lasers) allows for in situ dynamic instant analysis and reaction to the etching process. Representative examples of reflectance based measurements of etch rates are described in U.S. Pat. Nos. 6,406,641, 6,716,362, 7,019,850, and 7,306,696.

EXAMPLES

The foregoing may be better understood by reference to the following examples, which are presented for purposes of illustration and are not intended to limit the scope of the invention. In particular the examples demonstrate representative examples of principles innate to the invention and these principles are not strictly limited to the specific condition recited in these examples. As a result it should be understood that the invention encompasses various changes and modifications to the examples described herein and such changes and modifications can be made without departing from the spirit and scope of the invention and without diminishing its intended advantages. It is therefore intended that such changes and modifications be covered by the appended claims.

pH calibration buffer solutions were tested and optimized for accurate pH measurement using indicator dyes. Several pH sensitive color dye and their combination solutions were prepared and optimized as indicator solutions for pH measurements in the range of pH 5 to 7.5. This pH range will provide good linear responses to the change of low HF levels that are present in the 17% NH4F etch.

A number of color dye solutions were prepared including:
1. 0.05% w/v Phenol Red dye (PR) solution
2. 0.05% w/v Phenol Red dye (PR) solution in D.I. Water+1% v/v Isopropyl alcohol (IPA)
3. 0.016 w/v % Chlorophenol Red dye CPR) solution
4. 0.0142 w/v % Chlorophenol Red dye (CPR) solution in 0.5% v/v IPA
5. 0.0248 w/v % PR+0.01377 w/v % CPR solution
6. 0.0248 w/v % PR+0.0121 w/v % CPR in ~0.5% v/v IPA
7. 0.0231 w/v % Thymol Blue dye (TYB) solution
8. 0.0198 w/v % PR+0.0110 w/v % CPR+0.0046 w/v % TYB solution
9. 0.008 w/v % CPR+0.01155 w/v % TYB solution
10. 0.01 w/v % PR+0.01 w/v % CPR+0.008 w/v % TYB
11. 0.0138 w/v % PR+0.00945 w/v % CPR+0.0077 w/v % TYB A phosphate buffer stock (pH 7.3) was prepared from 6.8128 g $KH_2PO_4$, 1.5352 g NaOH, and 870 ml D.I. Water. pH was 7.3-7.32 and was calibrated with a pH meter. The stock was used to create a buffer calibration solution having a pH of between 6.0 and 7.2.

pH calibration was tested using Indicator Dye solutions and Phosphate Buffer Calibration Solutions. To the pH buffer solution was added 500 ul of dye solution, such as the 0.05 w/v % phenol red sodium salt pH indicator dye solution, to 10 ml of the phosphate buffer pH solutions in a 15 ml test tube. The tubes were tightly capped, mixed thoroughly, and left to allow the color to develop for a few minutes. A reference sample was prepared by mixing 500 ul of deionized water with 10 ml of the stock pH7.3 phosphate buffer solution.

The spectrometer instrument was zeroed using the reference sample for wavelength range approximately between 700-400 nm. Each buffer solution was scanned in the same wavelength and the data was saved. The absorbance spectrum of the pH buffer samples were compared, and the wavelength of interest was selected. For example, phenol red indicator dye has an absorption maximum at 558.9 nm which could be used as the absorbance of interest. If needed, the absorbance values can also be converted to percent transmittance (% T) for comparison or calibration.

The Absorbance (or % T) was plotted on the x-axis versus the pH of the phosphate buffer solution (y-axis). This is the pH indicator dye calibration curve. Using this curve, the pH of unknown solution can be determined. (Note: % T vs. pH may provide a more linear curve in some cases.)

Result and Discussion
A) pH Value of Calibration Buffer Solution

Accurate pH measurement is vital for the development of an automatic method to measure HF concentrations in Buffered Oxide Etch (BOE). The pH values of the calibration buffer solutions are commonly measured by laboratory pH meters. Since there are many different types and different manufacturers of pH meters available, their measurements and their repeat measurements may be slightly different from meter to meter. Table I below showed that the pH measurements obtained from a hand held pH meter and electrode (new type meter and electrode) that does not use a calibration process were about 0.1 pH unit less than those measured by a common laboratory meter with Inlab Expert Pro pH electrode that was calibrated with standard pH 4 and pH 7 buffers. Repeat measurement of the same solution using the laboratory meter also showed a slightly difference between measurements. About 0.01 to 0.04 pH unit difference was observed on 21 samples measured twice using the same meter. Therefore, pH of the calibration solutions are only accurate to +/−0.04 pH unit.

However, these differences could be due to the temperature variations in the laboratory. The pH meter that does not use a calibration process was used inside the hood in the process area showing a temperature during sample measurement about 20 C. Where as the lab meter showed a temperature of 21.7 C in the open lab.

Since pH of the calibration solutions are very critical to the overall SIA method, for quality control purposes, one should take appropriate steps to ensure the measurement of the pH calibration solutions are done properly and uniformly using a pH meter.

TABLE I

Comparison of pH Reading Obtained using Different pH Meter on Same Buffer Solution

| Meter #1 | Meter #2 read (1) | Meter #2 read (2) |
|---|---|---|
| 7.32 | 7.32 | 7.32 |
| 7.21 | 7.28 | 7.30 |
| 7.10 | 7.20 | 7.19 |
| 7.02 | 7.12 | 7.10 |
| 6.91 | 7.00 | 6.99 |
| 6.79 | 6.91 | 6.90 |

TABLE I-continued

Comparison of pH Reading Obtained using
Different pH Meter on Same Buffer Solution

| Meter #1 | Meter #2 read (1) | Meter #2 read (2) |
|---|---|---|
| 6.71 | 6.83 | 6.81 |
| 6.61 | 6.72 | 6.71 |
| 6.50 | 6.61 | 6.60 |
| 6.40 | 6.50 | 6.49 |
| 7.32 | 7.28 | 7.32 |
| 6.00 | 6.09 | 6.08 |
| 7.03 | 7.11 | 7.09 |
| 6.30 | 6.43 | 6.41 |
| 6.78 | 6.85 | 6.86 |
| 7.32 | 7.32 | 7.32 |
| 6.74 | 6.86 | 6.84 |
| 6.09 | 6.18 | 6.17 |
| 3.00 | 3.06 | 3.05 |
| 6.99 | 6.97 | 6.99 |
| 5.60 | 5.64 | 5.63 |

Figure 2:
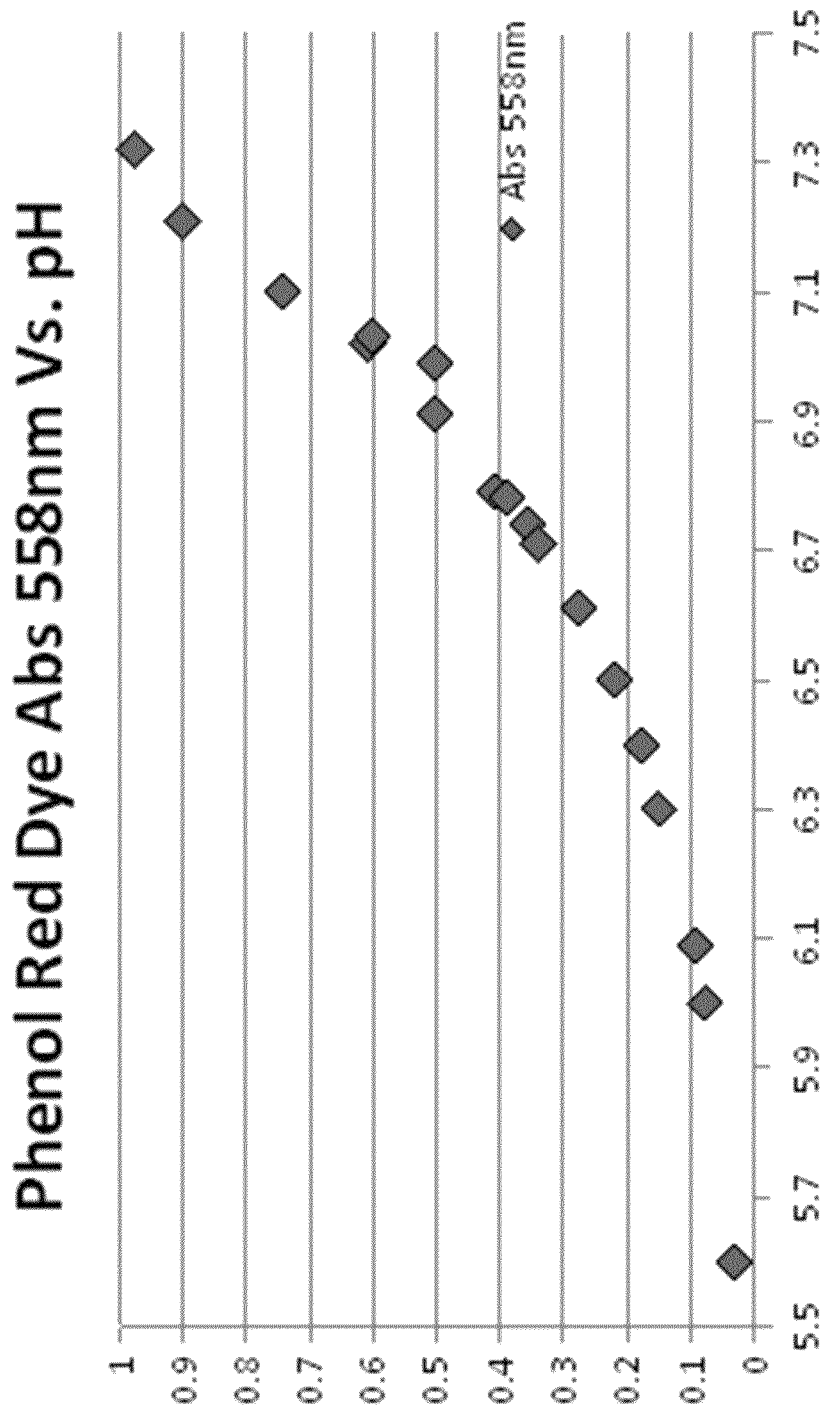
FIG. 2 is a graph illustrating the peak absorbance at 58 nm for pH range between 5.5 and 7.7 in increments of 0.1 pH unit.

Meter #1 - Nalco Waterproof pH/mv/oC meter with EUTECH Instrument electrode
No Calibration needed, electrode storage solution pH 6.32, Read Temp 20.7 C.
Calibration solutions read pH 7.01 and pH 3.96
Meter #2 - Mettler Toledo MP220 pH meter with Inlab Expert Pro pH electrode
Calibrated with pH7 and pH 4 buffer solutions, Read temp 21.7 C.
Note 1: pH readng between the two pH meter differ between 0.01 to 0.12 pH unit
Note 2: Repeat reading using same meter is differ between 0.01 to 0.04 pH unit B) Phenol Red Indicator Dye Spectra and pH Range Phenol Red indicator was evaluated for pH measurement using the phosphate buffered calibration solutions. FIG. 1 shows the visible spectra of this indicator in various pH buffers. FIG. 2 is the peak absorbance at 558 nm for pH range between 5.5 to 7.7 in inclement of 0.1 pH unit. We can see that this indicator dye only linear in the pH range between 6.7 to about 7.2. This dye may not be optimum for the low $NH_4F$ BOE application.

Figure 3:
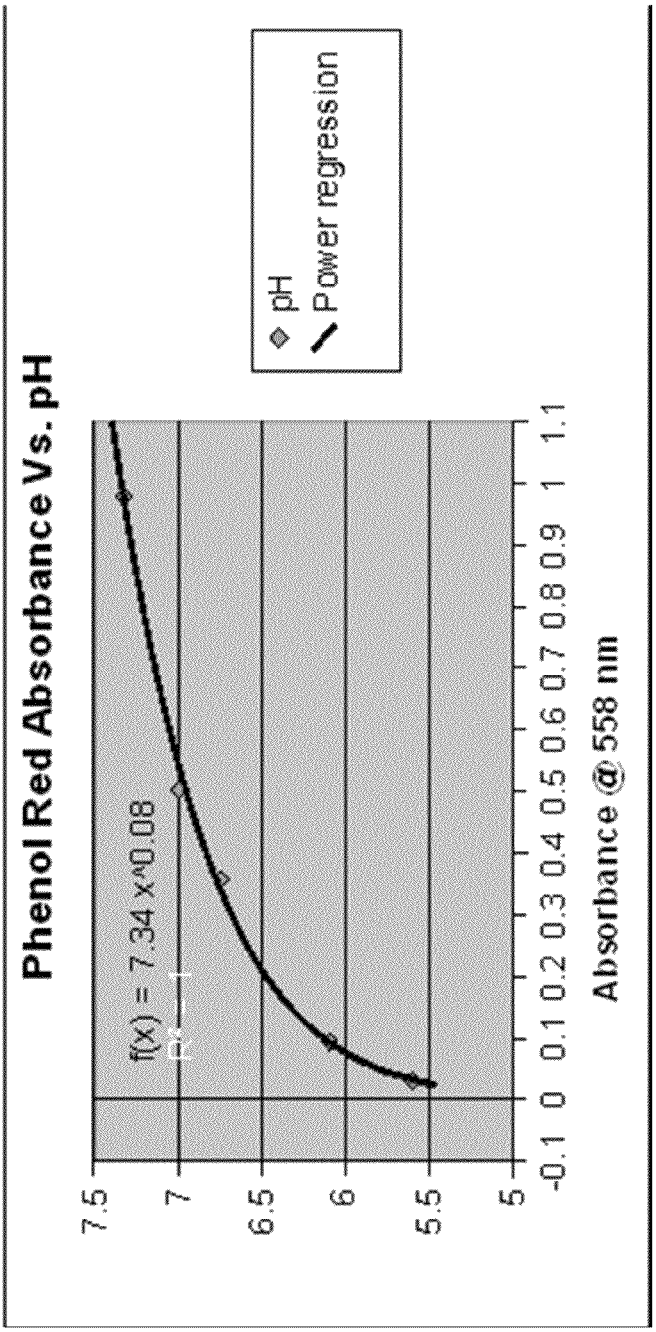
FIG. 3 is a graph illustrating that the calibration is a power regression for phenol red indicator dye.

FIG. 3 and Table II show that although the $R^2$ is about 1, the calibration is a power regression for phenol red indicator dye. Using this calibration, pH of some calibration standard solutions were determined and compared to the pH meter measurements (Table II). Results are very reasonable. It is desirable to improve the pH range. A linear calibration curve would be better for the HF determination with a very narrow spec in the BOE application.

TABLE II

Comparison of pH Meter Reading
and Phenol Red Dye Determination
Using 558 nm Absorbance value for calibration

| 558 nm | pH (meter) | pH (PR dye) |
|---|---|---|
| 0.935 | 7.21 | 7.30 |
| 0.742 | 7.10 | 7.17 |
| 0.61 | 7.02 | 7.06 |
| 0.502 | 6.91 | 6.95 |
| 0.409 | 6.79 | 6.84 |
| 0.339 | 6.71 | 6.74 |
| 0.276 | 6.61 | 6.64 |
| 0.219 | 6.50 | 5.52 |
| 0.177 | 6.40 | 6.41 |
| 0.077 | 6.00 | 6.01 |
| 0.601 | 7.03 | 7.05 |
| 0.15 | 6.30 | 6.33 |
| 0.389 | 6.78 | 6.82 |

C) Chlorophenol Red (CPR) Indicator Dye Spectra and pH Range

Figure 4:
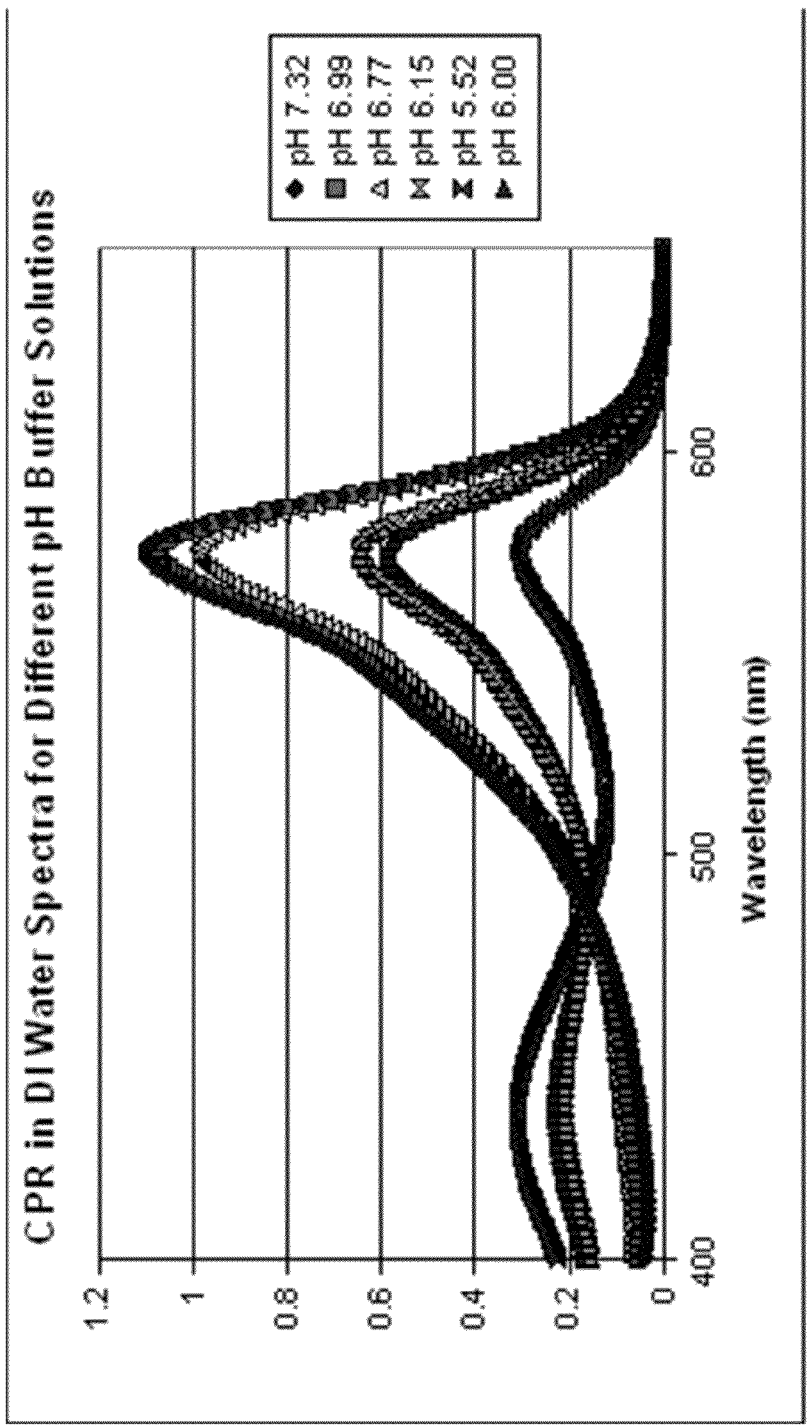
FIG. 4 is a graph illustrating the visible spectra of chloroprene red indicator dye for pH range from pH 5.5 to 7.32.
Figure 5:
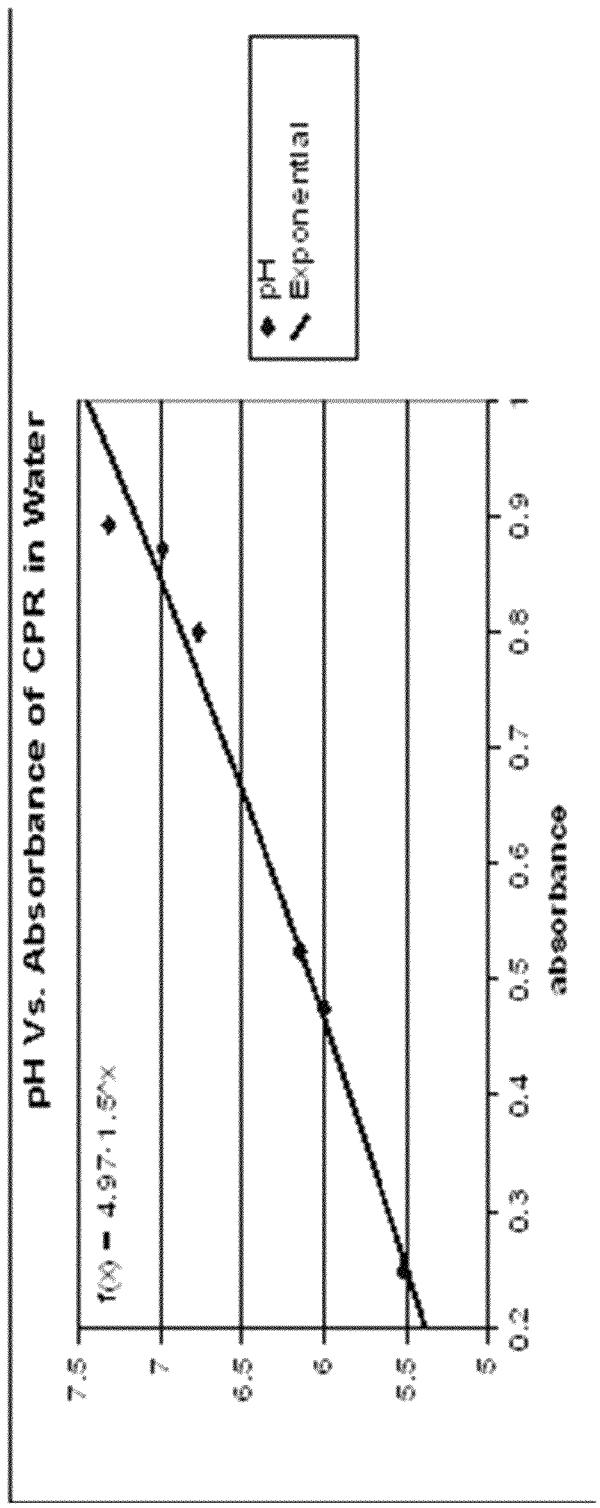
FIG. 5 is a graph illustrating the plot of absorbance average of 6 wavelengths vs. pH.

FIG. 4 is the chloroprene red indicator dye visible spectra for pH range from pH 5.5 to 7.32. FIG. 5 shows a plot of absorbance average of 6 wavelengths vs. pH. A linear response was observed with $R^2$=0.998. However, this good linearity only applies up to a pH of 7. This could be due to low dye concentration (0.0162 w/v %) which was used in the study. This dye showed good potential extending to the lower pH region.

D) Combination of Phenol Red and Chlorophenol Red Dyes as Indicator of pH Measurement From the above data and results, a mixture of 0.0248 w/v % PR and 0.0138 w/v % CPR was evaluated. Very good linear responses was observed for pH 5.5 to pH 7.3. This mixture performs well in an SIA application.

E) Mixture of Chlorophenol Red and Thymol Blue as Indicator Dye for pH Measurement To extend the linearity of the upper pH area, 0.0116 w/v % Thymol blue dye combined with 0.0081 w/v % CPR dye was evaluated. Due to the low concentration of the PCR dye, good linearity is only up to a pH of about 7.

Figure 6:
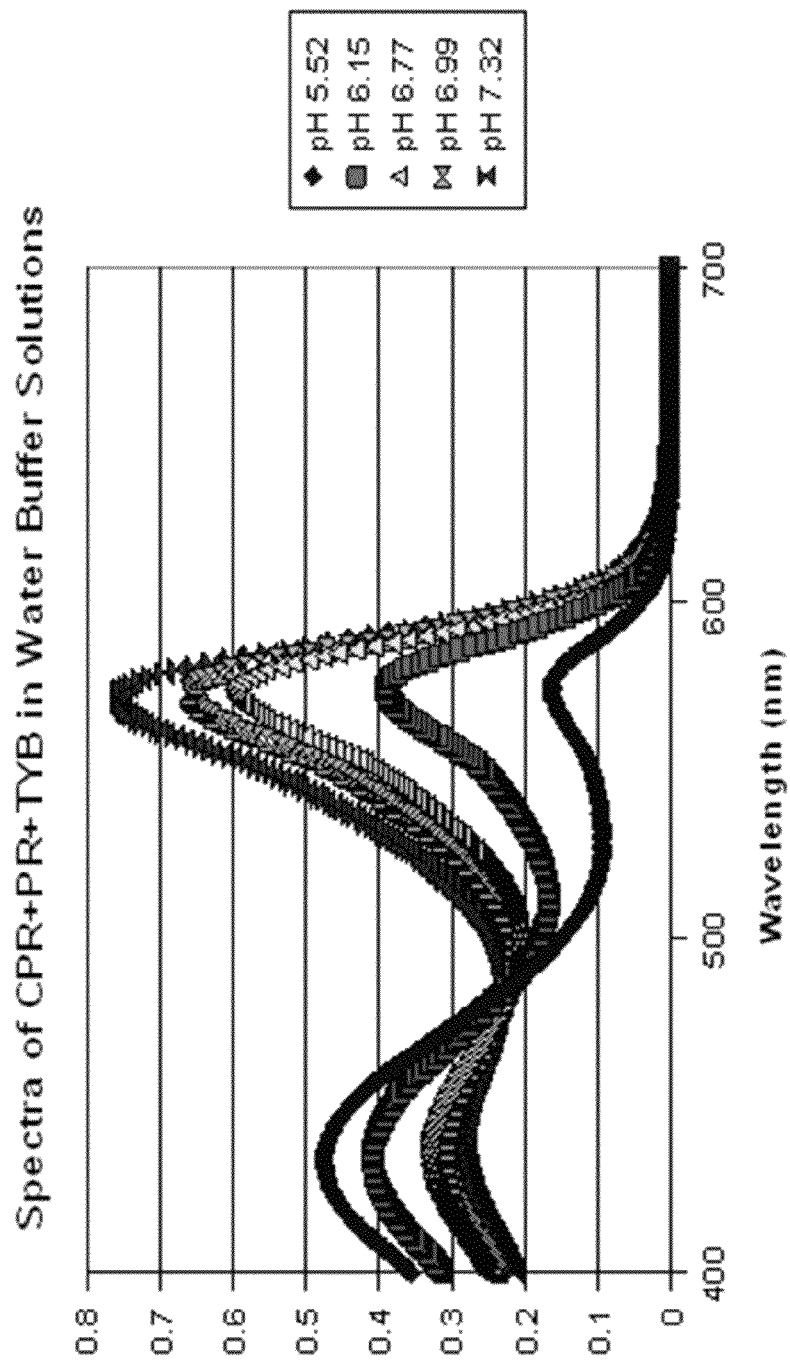
FIG. 6 is a graph illustrating the spectra and calibration of PR+CPR+TYB.
Figure 7:
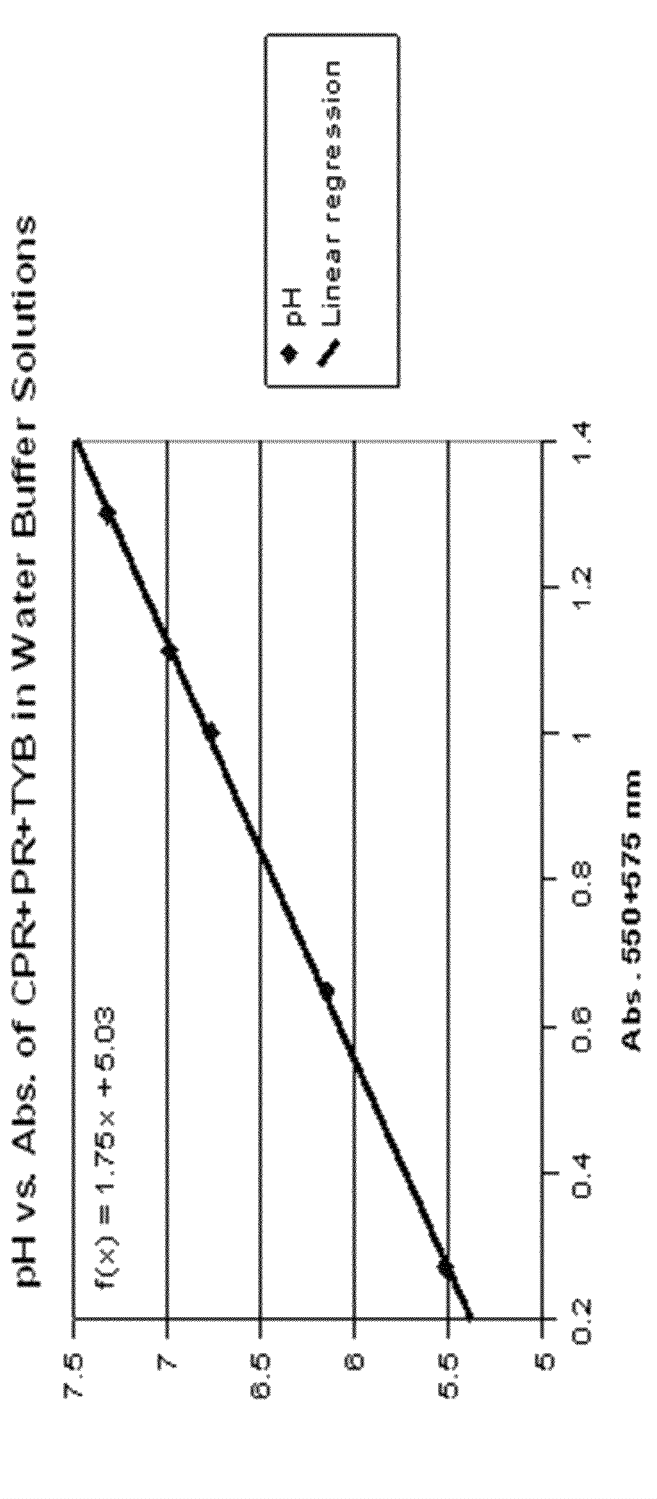
FIG. 7 is a graph illustrating the absorbance decrease with increasing pH of PR+CPR+TYB.

F) Mixture of Phenol Red, Chlorophenol Red and Thymol Blue as Indicator Dye for pH Measurements Since mixture of PR+CPR works very well as an indicator for pH measurement, to further explore the range of linear application, Thymol blue (TYB) was added to the mixture. FIG. 6 and FIG. 7 are the spectra and calibration of the best combination. The indicator contains about 0.0100% of PR, 0.0100% of CPR and 0.0081% of TYB. With this indicator dye mix, a linear calibration was obtained for pH range from 5.5 to 7.3 (FIG. 6) with $R^2$=0.9996. This dye mixtures is definite a good candidate for the SIA application. In addition, there are two region of the spectra can be used for measurement. One is at the peak area around 575 nm such as the sum of absorbance at 550 nm+575 nm (FIG. 6). The other area is around 435 nm. In this area, the absorbance decrease with increasing pH (FIG. 7). It is also linear. This can be used for pH confirmation check.

Reproducibility study on this triple combination indicator dye was evaluated. A new dye solution with variation slightly in the PR concentration of about 0.014% was prepared and tested. The same linear curve on absorbance vs. pH was observed. The reproducibility of this mixture is very good. New calibration buffer solution was also prepared and tested using the new indicator dye solution.

Table III summarizes all the indicator dyes and their combinations that were evaluated for the HF/SIA application. The best candidates are:

1) 0.0248 w/v % PR+0.0138 w/v % CPR 2) 0.0100 w/v % PR+0.0100 w/v % CPR+0.0081 w/v % TYB 3) 0.00138 w/v % PR+0.0095 w/v % CPR+0.0077 wv % TYB 4) 0.0200 w/v % PR+0.0200 w/v % CPR+0.0100 w/v % TYB

For SIA application, a more concentrated indication dye solution will be an advantage because less reagent will be consumed. Therefore, the following combination would be a good useful choice also.

TABLE III

Summary Data on All the Indicator Dyes and Their Combinations

Data on Indicator Dye Solutions

| Indicator Dye Solution | | w/v % in DI water | PR/CPR Ratio | Linear pH Range | R^2 | Equation | |
|---|---|---|---|---|---|---|---|
| PR | | 0.0492 | | 6.6-7.3 | 0.9989 | y = 7.3379X^0.0781 | power |
| PR + CPR | PR | 0.0248 | 1.8/1 | 5.5-7.3 | 0.9967 | y = 2.113x + 5.0768 | linear |
| | CPR | 0.0138 | | | | | |
| | Total | 0.0386 | | | | | |
| CPR | | 0.0162 | | 5.5-7.0 | 0.998 | y = 2.3416x + 4.9176 | linear |
| CPR + TYB | CPR | 0.0081 | | 5.5-7.0 | 0.9957 | y = 4.656x + 4.9688 | linear |
| | TYB | 0.0116 | | | | | |
| | Total | 0.0197 | | | | | |
| CPR + PR + TYB | CPR | 0.0110 | 1.8/1 | 5.5-7.3 | 0.9955 | y = 2.631x + 5.1355 | linear |
| | PR | 0.0198 | | | | | |
| | TYB | 0.0046 | | | | | |
| | Total | 0.0354 | | | | | |
| CPR + PR + TYB (new dye solution) | CPR | 0.0095 | 1.45/1 | 5.5-7.3 | 0.9966 | y = 1.5048x + 5.1551 | linear |
| | PR | 0.0138 | | | | | |
| | TYB | 0.0077 | | | | | |
| | Total | 0.0310 | | | | | |
| CPR + PR + TYB (new dye solution) (new buffer solution) | CPR | 0.0095 | 1.45/1 | 5.5-7.3 | 0.9956 | y = 1.6238x + 5.0644 | linear |
| | PR | 0.0138 | | | | | |
| | TYB | 0.0077 | | | | | |
| | Total | 0.0310 | | | | | |
| CPR + PR + TYB | CPR | 0.0100 | 1/1 | 5.5-7.3 | 0.9996 | y = 1.754x + 5.0296 | linear |
| | PR | 0.0100 | | | | | |
| | TYB | 0.0081 | | | | | |
| | Total | 0.0281 | | | | | |

G) Solvent for Indicator Dye Solution

Figure 8:
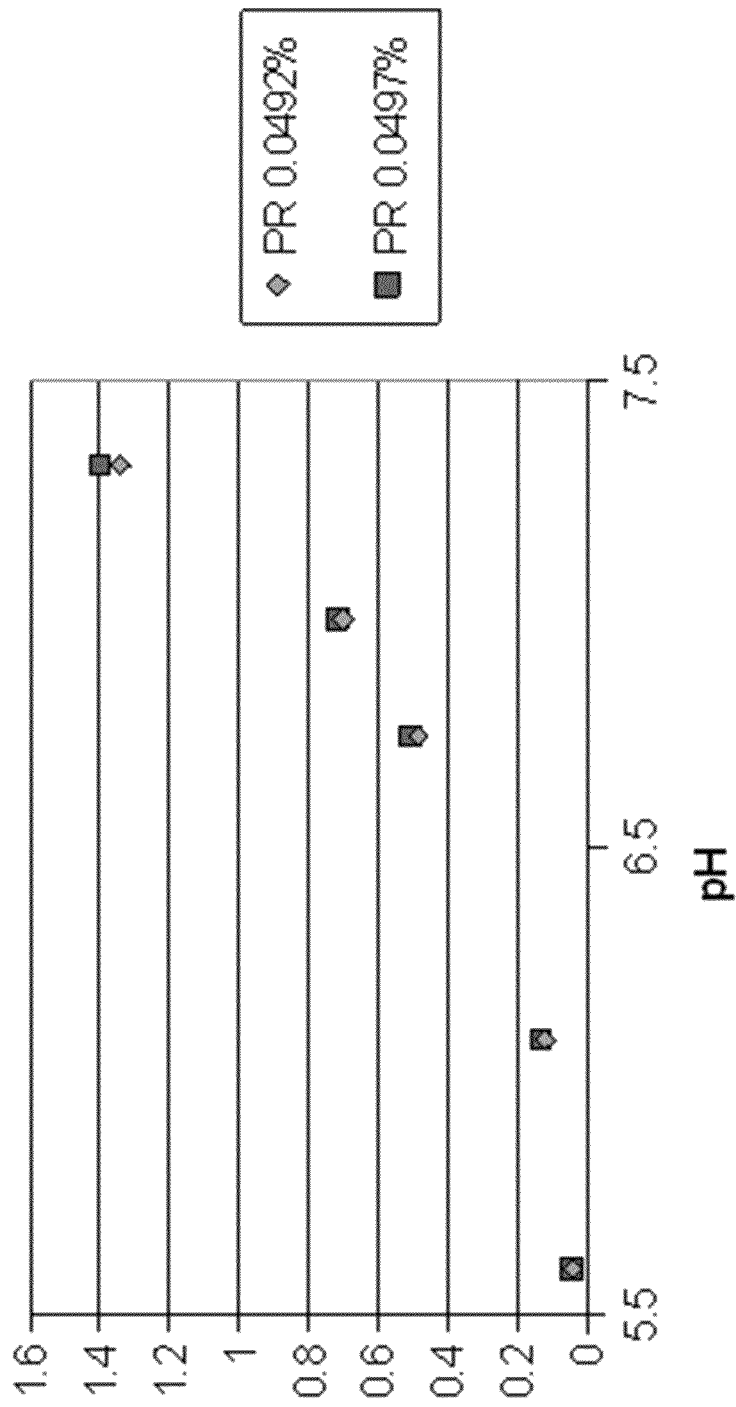
FIG. 8 is a graph illustrating that the indicator dye has similar absorbance with and without IPA present in the solution.
Figure 9:
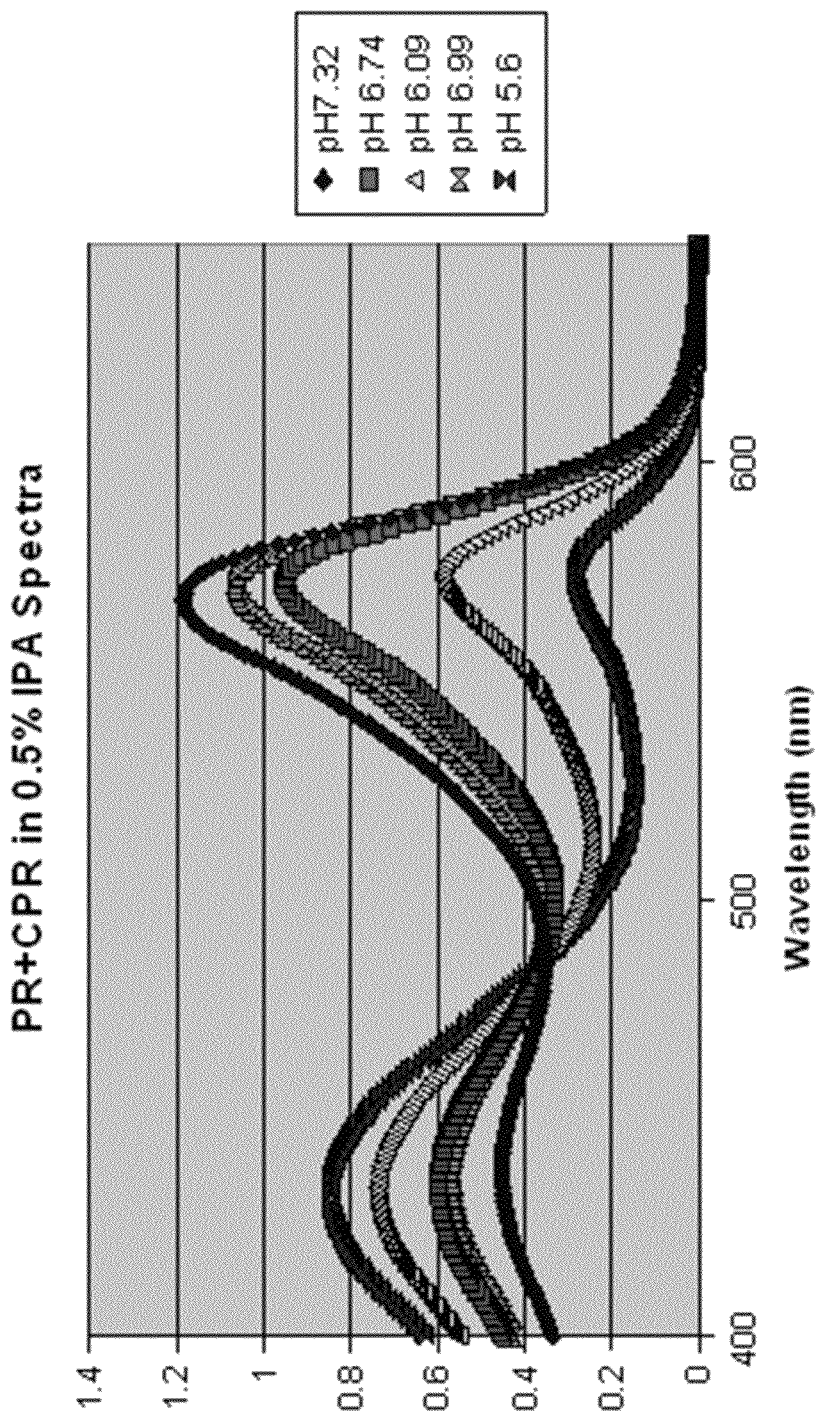
FIG. 9 is a graph illustrating that in the presence of 0.5% IPA, the visible spectra of PR+CPR are the same as the dyes in D.I. water.

Most indicator dyes are very soluble in D.I. water. Some have to be stirred for a while to dissolve. All the studies above are done with indicator dyes dissolved in D.I. water. To prevent unexpected staining which may happen sometimes on surfaces during prolonged use, a study was conducted to add small amount of alcohol to the dye solution since most dyes are soluble in alcohol. Phenol Red dye and its combination to CPR were used for the study. FIG. 8 shows that the indicator dye has similar absorbance with and without IPA present in the solution. FIG. 9 shows that in the presence of 0.5% IPA, the visible spectra of PR+CPR are the same as the dyes in D.I. water. Table IV compares the absorbance of 550 nm+575 nm for pH buffer between 5.5 and 7.3 for PR dye solution with and without 1 v/v % IPA. No major difference was observed. Therefore, if needed, a small amount of isopropyl alcohol can be added to the dye solution to prevent unexpected color staining problem on surface that may occur during prolonged use of the indicators.

TABLE IV

Comparison of Phenol Red dye solution with and without 1% v/v IPA

| 550nm + 575 nm pH | PR 0.0492%+IPA | PR 0.0497% |
|---|---|---|
| 7.32 | 1.342 | 1.400 |
| 6.74 | 0.487 | 0.512 |
| 6.09 | 0.124 | 0.136 |
| 6.99 | 0.704 | 0.719 |
| 5.6 | 0.043 | 0.047 |

The results demonstrate that several pH sensitive color dyes and their combinations are useful for measuring pH and indirectly measuring HF level and NH4F level in BOE. Phenol red (PR), Chlorophenol Red (CPR) dyes work well by themselves for the application. However, these indicators by themselves only provide good pH measurements in the range of pH 5 to pH7. This range is not sufficient for low NH4F level BOE. Additionally, absorbances of PR are non-linear in the pH range of 5 to 7.5. A power regression curve has to be used for calibration. Early feasibility study showed that it is necessary to obtain good linearity in the pH range of 5 to 7.5 for low level HF determination in low concentration NH4F buffered etch. Therefore a combination of indicator dyes was explored to extend the linearity. Mixture of Chlorophenol Red dye with other pH sensitive indicator dyes were developed to extend the upper and lower pH range and to improve the detection sensitivity. The mixture of indicators are: PR+CPR, CPR+Thymol Blue, PR+CPR+Thymol Blue. These combinations of indicator dyes worked well and will provide good linearity and needed sensitivity for the automated SIA application of HF detection in BOE matrix.

While this invention may be embodied in many different forms, those described in detail herein specify preferred embodiments of the invention. The present disclosure is an exemplification of the principles of the invention and is not intended to limit the invention to the particular embodiments illustrated. All patents, patent applications, scientific papers, and any other referenced materials mentioned herein are incorporated by reference in their entirety. Furthermore, the invention encompasses any possible combination of some or all of the various embodiments described herein and/or incorporated herein. In addition the invention encompasses any possible combination that also specifically excludes any one or more of the various embodiments described herein and/or incorporated herein.

The above disclosure is intended to be illustrative and not exhaustive. This description will suggest many variations and alternatives to one of ordinary skill in this art. The compositions and methods disclosed herein may comprise, consist of, or consist essentially of the listed components, or steps. As used herein the term "comprising" means "including, but not limited to". As used herein the term "consisting essentially of" refers to a composition or a method that includes the disclosed components or steps, and any other components or steps that do not materially affect the novel and basic characteristics of the compositions or methods. For example, compositions that consist essentially of listed ingredients do not contain additional ingredients that would affect the properties of those compositions. Those familiar with the art may recognize other equivalents to the specific embodiments described herein which equivalents are also intended to be encompassed by the claims.

All ranges and parameters disclosed herein are understood to encompass any and all subranges subsumed therein, and every number between the endpoints. For example, a stated range of "1 to 10" should be considered to include any and all subranges between (and inclusive of) the minimum value of 1 and the maximum value of 10; that is, all subranges beginning with a minimum value of 1 or more, (e.g. 1 to 6.1), and ending with a maximum value of 10 or less, (e.g. 2.3 to 9.4, 3 to 8, 4 to 7), and finally to each number 1, 2, 3, 4, 5, 6, 7, 8, 9, and 10 contained within the range.

All numeric values are herein assumed to be modified by the term "about," whether or not explicitly indicated. The term "about" generally refers to a range of numbers that one of skill in the art would consider equivalent to the recited value (i.e., having the same function or result). In many instances, the term "about" may include numbers that are rounded to the nearest significant figure. Weight percent, percent by weight, % by weight, wt %, and the like are synonyms that refer to the concentration of a substance as the weight of that substance divided by the weight of the composition and multiplied by 100. Percentages and ratios are by weight unless otherwise so stated.

As used in this specification and the appended claims, the singular forms "a," "an," and "the" include plural referents unless the content clearly dictates otherwise. Thus, for example, reference to a composition containing "a compound" includes a mixture of two or more compounds. As used in this specification and the appended claims, the term "or" is generally employed in its sense including "and/or" unless the content clearly dictates otherwise.

This completes the description of the preferred and alternate embodiments of the invention. Those skilled in the art may recognize other equivalents to the specific embodiment described herein which equivalents are intended to be encompassed by the claims attached hereto.

What is claimed is:

1. A method of detecting and measuring the presence of ammonium fluoride in a BOE composition, the method comprising the steps of:
    collecting a representative sample of a BOE composition,
    adding a chromogenic agent to the composition,
    performing a spectrometric measurement of the composition,
    comparing the spectrometric measurement to pre-determined values to identify the quantity of ammonium fluoride in the BOE composition.

2. The method of claim 1 in which the BOE composition is a mixture of at least two different sources of BOE composition and the amount of ammonium fluoride in the composition cannot be determined by stoichiometry because the total amounts of ammonium fluoride mixed and/or volumes mixed are not known.

3. The method of claim 2 in which the BOE composition further comprises free HF and one of: $HNO_3$, $H_2SiF_6$, and $NH_4F$ and any combination thereof and the equilibrium amount of free HF in relationship to $HNO_3$, $H_2SiF_6$, and $NH_4F$ varies so the amount of free HF cannot be determined by stoichiometry.

4. The method of claim 2 in which the chromogenic agent is phenol red, chlorophenol red, thymol blue, bromocresol blue, rose Bengal, 4,5,6,7-Tetrachloro-2',4',5',7'-tetraiodofluorescein disodium salt, and any combination thereof.

5. The method of claim 4 in which the spectrometric measurement involves detecting of absorption peaks of emitted visible, infrared, and ultraviolet light at about 420 and 600 nm.

6. The method of claim 4 in which the spectrometric measurement involves detecting of absorption peaks at specific pre-determined wavelengths of infrared, visible, and/or ultraviolet light emitted into the BOE composition.

7. The method of claim 6 in which the intensity of at least one of the detected peaks is mathematically related to the amount of ammonium fluoride present in the first liquid.

8. The method of claim 2 in which the measurement involves an SIA analysis of a sample of BOE liquid used in an etching process on a wafer substrate.

9. The method of claim 8 in which the BOE composition further comprises a surfactant and the concentration of surfactant is determined by a spectrographic analysis.

10. The method of claim 9 in which the amount of BOE composition added to the etching process is adjusted so that an exact amount of ammonium fluoride and surfactant is applied to the wafer substrate.

11. The method of claim 10 in which the spectrographic analysis comprises the steps of:
    a. adding a surfactant to a process for making a microelectronic component, wherein an absorbance of the surfactant is capable of being measured, wherein the absorbance is ultraviolet-visible absorbance;
    b. sampling fluid from the process, the sampling performed subsequent to the addition of the surfactant to the process and also before application of the surfactant to the microelectronic component, the sampling performed by drawing the sample into a side stream comprising a flow cell;
    c. measuring the absorbance of the surfactant in the sample;
    d. correlating the absorbance of the surfactant in the sample with the concentration of the surfactant in the process; and
    e. taking action to maintain the concentration of the surfactant in the process at a level where the dilution ratio of about 200 parts total BOE composition volume to about one part surfactant volume; and wherein the chromogenic agent comprises 4,5,6,7-Tetrachloro-2',4',5',7'-tetraiodofluorescein disodium salt.

12. A method of detecting and measuring the presence of ammonium fluoride in a BOE composition, the method comprising the steps of:
    collecting a representative sample of a BOE composition,
    adding a chromogenic agent to the composition,
    performing a spectrometric measurement of the composition,
    comparing the spectrometric measurement to pre-determined values to identify the quantity of ammonium fluoride in the BOE composition;

wherein the measurement involves an SIA analysis of a sample of BOE liquid used in an etching process on a wafer substrate; and wherein the chromogenic agent is phenol red, chlorophenol red, thymol blue, bromocresol blue, rose Bengal, 4,5,6,7-Tetrachloro-2',4',5',7'-tetraiodofluorescein disodium salt, and any combination thereof.

* * * * *